(12) United States Patent
Näslund et al.

(10) Patent No.: US 7,348,578 B2
(45) Date of Patent: Mar. 25, 2008

(54) DEVICE AND METHOD FOR ELECTRON BEAM IRRADIATION

(75) Inventors: Lars Åke Näslund, Furulund (SE); Tommy Nilsson, Svedala (SE); Luca Poppi, Formigine (IT); Paolo Benedetti, Modena (IT); Anna Eriksson, Rydebäck (SE); Filippo Ferrarini, Modena (IT)

(73) Assignee: Tetra Laval Holdings & Finance S.A., Pully (CH)

( * ) Notice: Subject to any disclaimer, the term of this patent is extended or adjusted under 35 U.S.C. 154(b) by 274 days.

(21) Appl. No.: 10/555,759

(22) PCT Filed: Jun. 8, 2004

(86) PCT No.: PCT/SE2004/000891

§ 371 (c)(1),
(2), (4) Date: Nov. 7, 2005

(87) PCT Pub. No.: WO2004/110868

PCT Pub. Date: Dec. 23, 2004

(65) Prior Publication Data

US 2006/0284111 A1    Dec. 21, 2006

(30) Foreign Application Priority Data

Jun. 19, 2003    (SE) .................................... 0301782

(51) Int. Cl.
*H01J 37/30* (2006.01)
*G21F 7/00* (2006.01)
*G01N 23/00* (2006.01)

(52) U.S. Cl. ............................... 250/492.3; 250/515.1; 250/455.11

(58) Field of Classification Search ............. 250/492.3, 250/455.11, 515.1
See application file for complete search history.

(56) References Cited

U.S. PATENT DOCUMENTS 4,035,981 A    7/1977   Braun et al.

(Continued)

FOREIGN PATENT DOCUMENTS

GB          1 353 831          5/1974

(Continued)

*Primary Examiner*—Jack I. Berman
*Assistant Examiner*—Johnnie L Smith, II
(74) *Attorney, Agent, or Firm*—Buchanan, Ingersoll & Rooney PC

(57) ABSTRACT

The present invention refers to a device for electron beam irradiation of at least a first side of a web, the device comprising a tunnel through which the web is adapted to pass, said tunnel being provided with a web inlet portion, a web outlet portion and a central portion adapted to receive at least a first electron beam emitter provided with an electron exit window through which electrons are adapted to be emitted into the tunnel. The tunnel is being angled at least two locations in each of the inlet portion and the outlet portion in such a way that any X-ray formed during the electron beam irradiation of the web is forced to hit the tunnel wall at least twice before exiting the tunnel.

20 Claims, 5 Drawing Sheets

U.S. PATENT DOCUMENTS

| | | | |
|---|---|---|---|
| 4,252,413 A | | 2/1981 | Nablo |
| 4,410,560 A | * | 10/1983 | Kosterka ................. 250/515.1 |
| 4,521,445 A | * | 6/1985 | Nablo et al. ............. 250/492.3 |
| 5,120,972 A | * | 6/1992 | Rangwalla et al. ...... 250/492.3 |
| 5,194,742 A | * | 3/1993 | Avnery et al. ........... 250/492.3 |
| 5,473,164 A | * | 12/1995 | Klenert et al. ........... 250/492.3 |
| 6,727,508 B1 | * | 4/2004 | Tominaga et al. ....... 250/492.1 |
| 6,749,903 B2 | * | 6/2004 | Weiss et al. ................ 427/496 |
| 2001/0035500 A1 | * | 11/2001 | Schianchi et al. ..... 250/455.11 |
| 2004/0089820 A1 | * | 5/2004 | Rangwalla et al. ...... 250/492.3 |
| 2006/0145093 A1 | * | 7/2006 | Naslund et al. .......... 250/492.1 |
| 2007/0205381 A1 | * | 9/2007 | Nakao ..................... 250/492.3 |

FOREIGN PATENT DOCUMENTS

| | | |
|---|---|---|
| GB | 2 157 140 | 10/1985 |
| JP | 2000-214300 | 8/2000 |
| JP | 2000-214300 A | 8/2000 |
| JP | 2002-171949 A | 6/2002 |

* cited by examiner

DEVICE AND METHOD FOR ELECTRON BEAM IRRADIATION

This application is based on and claims priority to Swedish Application No. 0301782-9 filed Jun. 19, 2003 and International Application No. PCT/SE2004/000891 filed on Jun. 8, 2004 designating the U.S., the entire contents of both of which are hereby incorporated by reference.

THE FIELD OF INVENTION

The present invention refers to a device and a method for electron beam irradiation of at least a first side of a web.

PRIOR ART

Within the food packaging industry it has for a long time been used packages formed from a web of packaging material comprising different layers of paper or board, liquid barriers of for example polymers and gas barriers of for example thin films of aluminium. In the packaging machine the web is formed into a tube by overlappingly sealing the longitudinal edges of the web. The tube is continuously filled with a product and then transversally sealed and formed into cushions. The cushions are separated and formed into for example parallelepipedic containers. This technology of forming a tube from a web is well known per se and will not be described in detail.

To extend the shelf-life of the products being packed it is prior known to sterilise the web before the forming and filling operations. Depending on how long shelf-life is desired and whether the distribution and storage is made in chilled or ambient temperature, different levels of sterilization can be choosen. One way of sterilising a web is chemical sterilization using for example a bath of hydrogen peroxide. Another way is to irradiate the web by electrons emitted from an electron beam emitter. Such an emitter is disclosed in for example U.S. Pat. No. 5,194,742.

However, irradiation with electrons creates unwanted X-rays. The electrons are slowed down as they collide with amongst others air molecules, bacteria, the web and the walls of the shielding. This decrease of the speed of the electrons gives rise to the emission of X-rays. When such an X-ray hits the shielding, the X-ray enters a certain distance into the material and causes emittance of new X-rays. It has been a problem to obtain acceptable radiation levels outside an irradiation device of reasonable size.

In GB 2 157 140, describing a device for continuous electron curing of inks, one way of solving the problem is shown. The emitter is placed in a central chamber through which the web is passed for treatment by the emitter. The central chamber is shielded and comprises a radiation trap for absorbing a substantial quantity of the radiation which remains unabsorbed by the web. At the entrance and exit of the central chamber first subchambers are provided. These first subchambers are provided with radiation traps for absorbing the radiation that escapes through the exit and entrance of the central chamber. At the openings of the subchambers which are located opposite the entrance and exit of the central chamber an acceptable radiation level has been obtained. The radiation traps in the first subchambers are formed as parallel protrusions extending from the inner walls thereof. Each function as a narrow "mail slot" through which the web is allowed to pass. Second subchambers are also provided which comprise plenums and exhaust means for introduction of inert gas to reduce the amount of oxygen passed on to the central chamber.

For altering the entrance and exit angels of the moving web in relation to the spacial positioning of the apparatus the subchambers are exchangeable. Thus, by removing one or more of the subchambers and replacing them with subchambers of a different geometry the angels can be changed without disturbing the central chamber.

However, when for example sterilising packaging material webs, within the food packaing industry, a solution according to GB 2 157 140 using radiation traps is not preferable. Firstly, due to the design of the radiation traps they may cause uncontrollable fluid flows through the irradiation device during sterilisation and cause difficulties during pre-sterilisation of the device itself. This may cause undesired and/or uncontrollable hygiene levels. Secondly, packaging material webs may be provided with pre-applied opening devices, such as caps, which protrudes from the web surface. Thus, the "mail slots" of the radiation traps need to be larger to let the web with caps pass. Larger slots give rise to less effective traps, and to obtain the same efficiency as with the narrow slots the number of traps may need to be increased. In turn the irradiation device gets larger and more bulky. Thus, for sterilization purposes within for example the food packaging industry, the problem of obtaining acceptable radiation levels outside an irradiation device of reasonable size still remains.

SUMMARY OF THE INVENTION

Therefore, an object of the invention has been to provide a device of reasonable size for electron beam irradiation where the radiation level outside the device is acceptable.

The object is achieved by a device for electron beam irradiation of at least a first side of a web, the device comprising a tunnel through which the web is adapted to pass, said tunnel being provided with a web inlet portion, a web outlet portion and a central portion adapted to receive at least a first electron beam emitter provided with an electron exit window through which electrons are adapted to be emitted into the tunnel, and whereby the tunnel being angled at at least two locations in each of the inlet portion and the outlet portion in such a way that any X-ray formed during the electron beam irradiation of the web is forced to hit the tunnel wall at least twice before exiting the tunnel. Thus, the invention comprises a shielding formed so that it is possible to pass a web through it, and still minimise the risk of X-rays being able to find their way out of the shielding, without first having their energy reduced to an acceptable limiting value. The limiting value can for example be settled by governmental regulations or market acceptance. Due to the fact that the tunnel design functions as a shielding, and reduces the energy of the X-rays, no radiation traps are necessary inside the tunnel. This provides for the possibility of being able to lead a controlled and undisturbed air flow through the device for ventilating and discharging for example ozone formed during irradiation. Further, such a controlled and undisturbed air flow provides the possibility of maintaining the sterilisation level during a stoppage of the packaging machine. This will be further descibed later.

In a preferred embodiment of the invention the inlet portion and the outlet portion respectively comprises three successive segments, an entrance segment, a central segment and an exit segment, and whereby the central segment forming a first angle to the entrance segment and the exit segment forming a second angle to the central segment. In this way both entrance and exit of the shielding are easily angled twice.

Preferably, the relation between the tunnel widths, said angles and the lengths of the segments is such that an imagined straight line hitting the tunnel wall in the entrance segment also hits the tunnel wall of at least the exit segment, before exiting the exit segment, and that an imagined straight line passing through the entrance segment hits the tunnel wall of the central segment such that it also hits the tunnel wall of at least the exit segment, before exiting the exit segment. By forcing the X-rays to hit the tunnel wall at least twice before exiting the shielding, an acceptable reduction of the energy of the X-rays are obtained. This will be explained in more detail below.

Advantageously, the central portion is adapted to receive an additional second electron beam emitter provided with an electron exit window through which electrons are adapted to be emitted into the tunnel, the electron beam emitter being adapted to be positioned so that the second side of the web is being irradiated by the electrons. By irradiating both sides of the web the risk of recontamination of the web is minimised, i.e. one avoid the risk of having bacteria from a non-sterilized side of the web being able to recontaminate a sterilized side.

Preferably, the electron exit window is substantially planar and adapted to be-provided substantially in parallell with the web. By emitting the electrons perpendicular to the web the distance that the electrons have to travel is minimised, which in turn minimises the loss of electron energy before the electrons reach the web. Further, the amount of electrons reaching the web is higher if the emitter is directed perpendicular to the web, which in turn leads to a better sterilization result.

In a further preferred embodiment the additional second electron beam emitter being adapted to be positioned substantially opposite the first electron beam emitter and the electron exit window being adapted to be positioned substantially opposite the first electron exit window. In this way both sides of the web are irradiated at the same time effectively minimising the risk of recontamination of the web.

In a yet further embodiment the emitter is enclosed in a housing. By providing a housing enclosing the emitter it is easier to encapsulate primary X-rays. Moreover, the housing enables a different pressure to be present around the emitters than the pressure present in the surrounding chamber. For example, the airflow through the device can thereby be more easily controlled.

In another embodiment the emitter being a low voltage electron beam emitter. Using a low voltage electron beam emitter minimises the risk of irradiation induced changes, such as for example product off-flavour, that can be derived from the package made by the irradiated web. Further, it goes without saying that a low voltage electron beam emitter gives rise to less energy consumption and less need for strong shielding, since the electrons and the X-rays have less energy. Further, the handling of X-rays and ozone ($O_3$) formed is simplified due to the relatively small amounts created in a low voltage electron beam emitter. Moreover, when using low voltage the emitter itself can be made relatively small.

In yet another preferred embodiment the inlet and outlet portions are each provided with at least one web guide for guiding the web through the tunnel. In this way guiding of the web is achieved in a simple way.

Preferably, the at least one web guide in the outlet portion is positioned in such a way with reference to the web that it is adapted to be in contact with a second side of the web, and that it is adapted to prevent contact with the first side of the web. By positioning the web guide in the outlet as described the first side of the web, which will later be in contact with the package content, will not be forced into contact with the web guide. This minimizes any eventual risk of negatively effecting the sterilized surfaces during the web handling in the outlet portion of the tunnel. Thus, the invention is suitable for use in the food packaging industry where relatively high sterilization levels must be guaranteed.

In an embodiment the web guide comprises a first and a second roller journalled in support members, the rollers being formed and mutually located in such a way that the first roller angles the web the second angle and the second roller angles the web the first angle. These rollers are reliable and relatively cheap.

In yet another embodiment the entrance segment of the inlet portion and the outlet portion are adjacent the central portion of the tunnel and that the exit segment of the inlet portion and the outlet portion are directed away from each other, thereby further separating the sterilized web from the non-sterilized web and thereby further minimising the risk of any recontamination.

Advantageously, the tunnel portions and the emitter housing are enclosed in a housing. This makes it easy to encapsulate, control and discharge ozone formed during irradiation.

Further, the invention refers to a method for electron beam irradiation of at least a first side of a web, the method comprising the steps of: passing the web through a tunnel, said tunnel being provided with a web inlet portion, a web outlet portion and a central portion adapted to receive at least a first electron beam emitter provided with an electron exit window, emitting electrons into the tunnel from the emitter through the electron exit window, and forcing any X-ray being formed by the electrons during irradiation of the web hit the tunnel wall at least twice before exiting the tunnel by forming the tunnel so that it is angled at at least two locations in each of the inlet and outlet portions. Thus, it is provided a way of shielding an irradiation device still making it possible to pass a web through it, and yet minimising the risk of X-rays being able to find their way out of the shielding, without first having their energy reduced to an acceptable limit value. Due to the fact that the tunnel design functions as a shielding, and reduces the energy of the X-rays, no radiation traps are necessary inside the tunnel. This provides for the possibility of being able to lead a controlled and undisturbed air flow through the device for ventilating and discharging for example ozone formed during irradiation. Further, such a controlled and undisturbed air flow provides the possibility of maintaining the sterilisation level during a stoppage of the packaging machine.

Preferably, the inlet portion and the outlet portion are formed so that the respective portion comprises a line of three successive segments, an entrance segment, a central segment and an exit segment, the central segment is made so that it forms a first angle to the entrance segment and so that the exit segment forms a second angle to the central segment. As mentioned before both the entrance and the exit of the shielding are easily angled twice in this way.

Advantageously, a relation between the tunnel widths, said angles and the lengths of the segments is provided so that an imagined straight line hitting the tunnel wall in the entrance segment is also hitting the tunnel wall of at least the exit segment, before exiting the exit segment, and that an imagined straight line passing through the entrance segment is hitting the tunnel wall of the central segment such that it is also hitting the tunnel wall of at least the exit segment, before exiting the exit segment. By forcing the X-rays to hit the tunnel wall at least twice before exiting the shielding, an acceptable reduction of the energy of the X-rays are obtained.

BRIEF DESCRIPTION OF THE DRAWINGS

In the following, a presently preferred embodiment of the invention will be described in greater detail, with reference to the enclosed drawings, in which.

DESCRIPTION OF PREFERRED EMBODIMENTS

Figure 1:
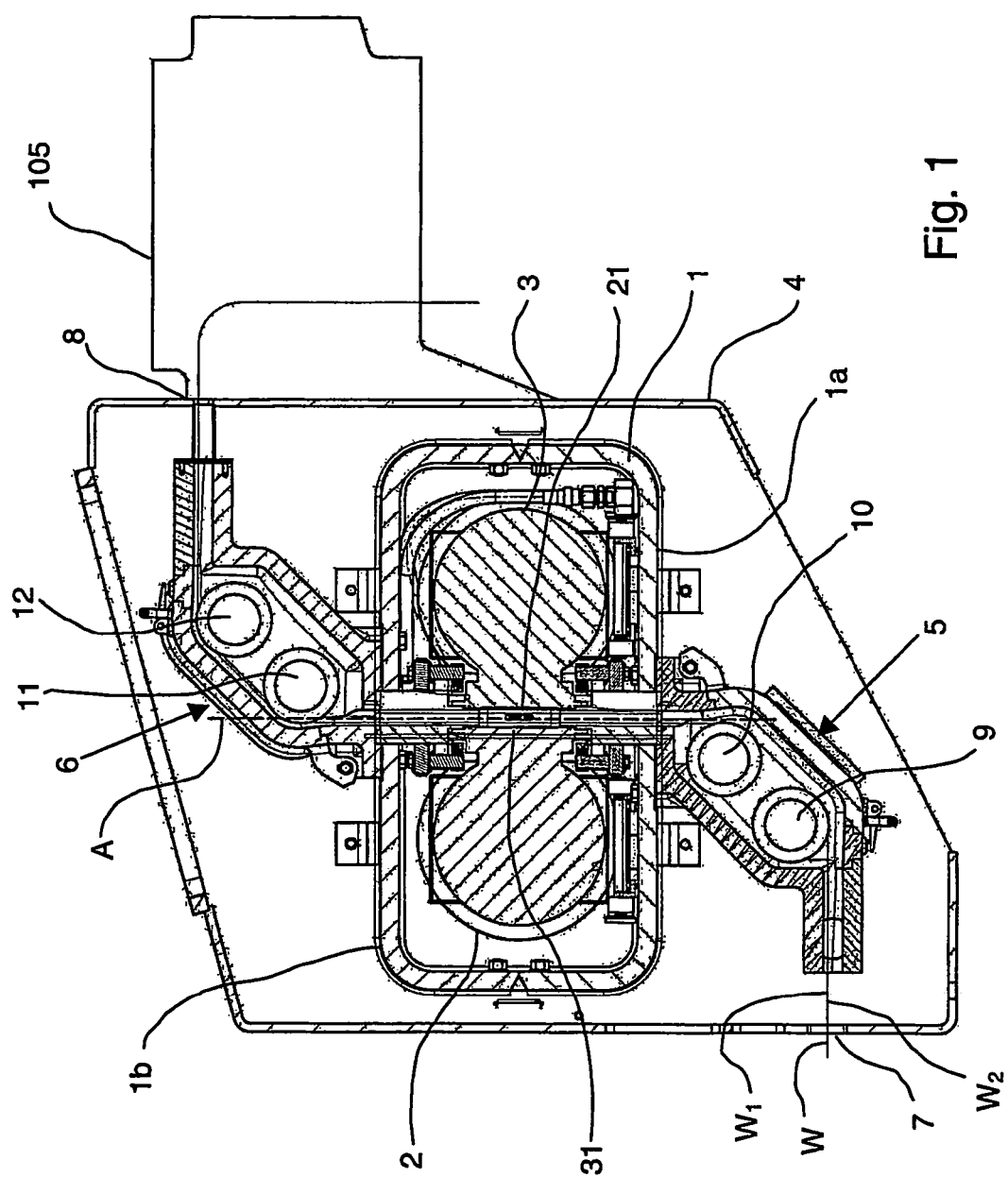
FIG. 1 shows a schematic cross section of the embodiment of the device.
Figure 3:
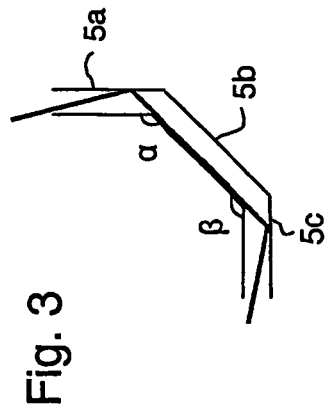
FIG. 3 shows a schematic first illustration on the relation between the tunnel widths, the angles and the lengths of the segments.
Figure 4:
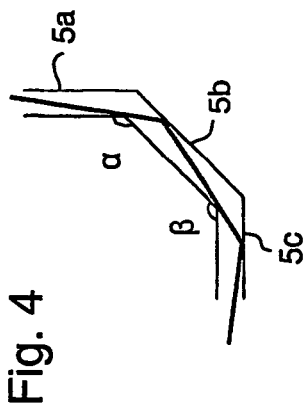
FIG. 4 shows a schematic second illustration on the relation between the tunnel widths, the angles and the lengths of the segments.
Figure 2:
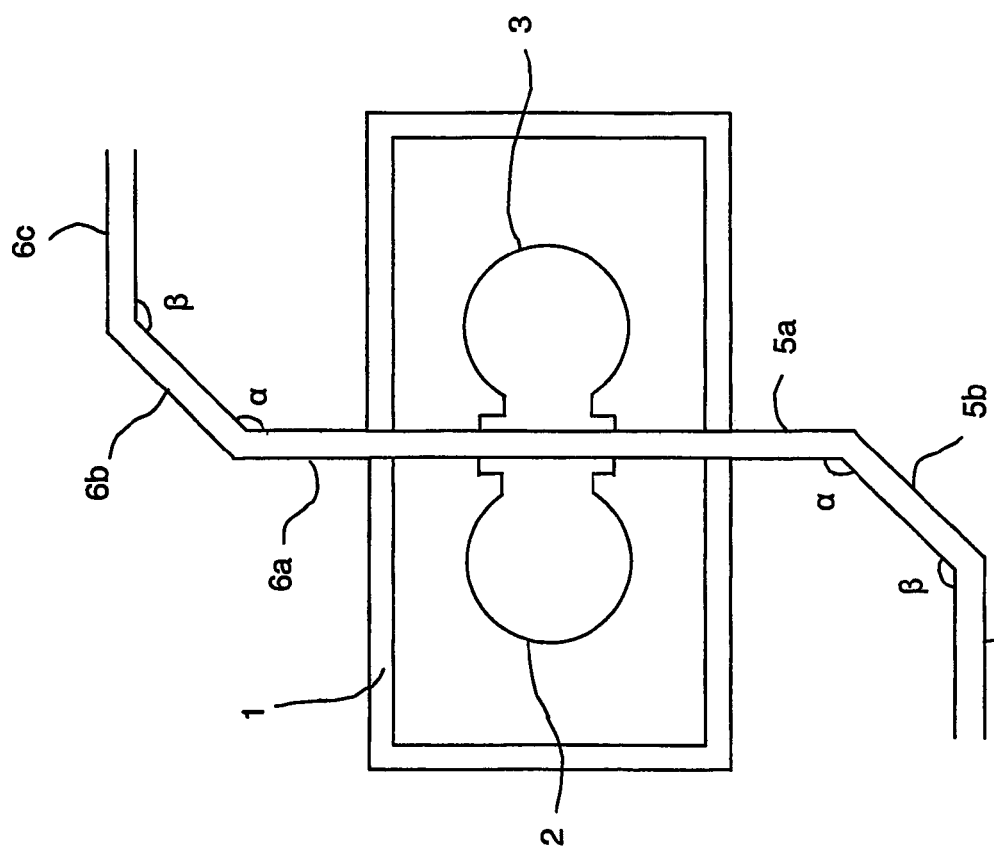
FIG. 2 shows a schematic view illustrating the segments of the tunnel, the angles and the inner housing with the emitters.

The device, shown in FIG. 1, comprises an inner housing 1 in which one or two emitters 2,3 are mounted. A central portion of the inner housing is adapted to receive the emitters. The inner housing 1 forms a tunnel and a packaging material web W is fed through the tunnel past the emitters 2,3. Further, the inner housing 1 is provided with an inlet portion 5 and an outlet portion 6 for the entrance and the exit of the web. The web inlet portion 5 is designed such that the inlet direction of the web W into the inlet portion 5 is angled in relation to the outlet direction of the web W out of the inlet portion 5. The outlet direction of the web W out of the inlet portion 5 is equal to the direction in which the web W passes the emitters 2,3. The angle between the inlet and the outlet direction of the web W in the inlet portion 5 is at least 90°. The inlet portion 5 is formed such that it is angled at at least two locations. In FIG. 2 is shown that the inlet portion 5 comprises three successive segments, an entrance segment 5a, a central segment 5b and an exit segment 5c. The central segment 5b forming a first angle α to the entrance segment 5a and the exit segment 5c forming a second angle β to the central segment 5b. Further, the relation between the tunnel widths, said angles α,β and the lengths of the segments 5a-c is such that an imagined straight line hitting the tunnel wall in the entrance segment 5a also hits the tunnel wall of at least the exit segment 5c, before exiting the exit segment 5c, and that an imagined straight line passing through the entrance segment 5a hits the tunnel wall of the central segment 5b such that it also hits the tunnel wall of at least the exit segment 5c, before exiting the exit segment 5c. In FIG. 3 and 4 are illustrated how the design can be obtained with help of paper, a ruler and a pen. In FIG. 3 a first worst case scenario is disclosed. A straight line is drawn beginning outside the entrace segment 5a and pointing substantially towards the outer corner between the entrance segment 5a and the central segment 5b. The line hits the tunnel wall in the entrance segment 5a and is drawn pointing substantially towards the inner corner between the central segment 5b and the exit segment 5c. If the relation between tunnel widths, angles α,β and segment lengths is to be considered good enough, the straight line will be forced to hit the tunnel wall of the exit segment 5c before exiting the exit segment 5c. In FIG. 4 a second worst case scenario is disclosed. A straight line is now drawn beginning outside the entrance segment 5a and pointing substantially towards the inner corner close to the exit of the entrance segment 5a, but is hitting the tunnel wall in the central segment 5b. The line is then drawn substantially towards the inner corner between the central segment 5b and the exit segment 5c. If the relation between tunnel widths, angles α,β and segment lengths is to be considered good enough, the straight line will be forced to hit the tunnel wall of the exit segment 5c before exiting the exit segment 5c. Thus, it is realised that if a certain angle is used, the parameters that can be modified are either the tunnel width or the length of the segment. A wide tunnel necessitates a long segment. If there is a need for a short segment, the tunnel width must be decreased. Another possibility is of course to change one or both of the angles. In the example shown the angles α and β, lengths and widths in the inlet portion are the same as the corresponding angles, lengths and widths in the outlet portion. It is to be understood that the angles as well as the lengths and the widths of the two portions can be different.

As has been previously mentioned, the web W passes the irradiation device 1, in which it is sterilized, and is subsequently fed into a sterile tower 105 of the filling machine where the web W is formed into a tube by overlappingly sealing the longitudinal edges of the web W. The tube is continuously filled with a product and then transversally sealed and formed into cushions. The cushions are separated and formed into for example parallelepipedic containers, i.e. packages. This technology of forming a tube from a web is well known per se and will not be further described.

The web W has two sides, a first side $W_1$ and a second side $W_2$. The first side $W_1$ of the web W is defined as being the side of the web W that is adapted to be in contact with the package content, i.e. the product, and that is adapted to become the inside of the tube during tube forming and thus the inside of the cushion, and subsequently the inside of the package once formed. Accordingly, the second side $W_2$ of the web W is thus defined as being the side of the web W that is not to be in contact with the product and that is adapted to become the outside of the tube during tube forming and thus the outside of the cushion, and subsequently the outside of the package once formed.

In the inlet portion the change in the running direction of the web W is accomplished by providing at least one web guide. In the example the web guide is a first and a second roller 9, 10 mounted inside the inlet portion 5. In the disclosed design the web W runs substantially horizontal into the inlet portion 5 and substantially vertically upwards when it leaves the inlet portion 5 and enters the inner housing 1. To accomplish this change in direction the rollers 9, 10 being formed and mutually located in such a way that the first roller 9 angles the web W the second angle β and that the second roller 10 angles the web W the first angle α. Preferably, the rollers 9, 10 are journalled in support members. The support members can for example be bearings provided with an outer shielding or with a bearing housing designed following the same design criteria as the tunnel.

The web W is fed through the inlet portion 5 in such a way that the first side $W_1$ of the web W is in contact with the web guide. Thus, during feeding, the first side $W_1$ will temporarily have contact with the envelope surfaces of the rollers 9, 10.

The outlet portion 6 is similarly designed with an entrance segment 6a, a central segment 6b and an exit segment 6c. To change the running direction of the web W the outlet portion 6 comprises one or more rollers 11, 12. The inlet portion 5 and the outlet portion 6 are mounted and designed such that the web W runs in the same direction as it leaves the outlet portion 6 as it does as it enters the inlet portion 5. In the disclosed design the inlet portion 5 and the outlet portion 6 are identical and mounted to two opposite faces 1a, 1b of the inner housing 1 using the same flange on respective portion 5, 6 but turned 180° about an axis A extending along the centre line of the web W running through the inner housing 1. Thus, the respective entrance segment 5a, 6a of the inlet portion 5 and the outlet portion 6 are adjacent the central portion of the tunnel and that the respective exit segment 5c, 6c of the inlet portion 5 and the outlet portion 6 are directed away from each other. Having an outlet portion 6 that is similar to the inlet portion 6 is advantageous in that the same mould can be used during manufacturing of the irradiation device 1.

In FIG. 1 it can be seen that the design of outlet portion 6 in relation to the inlet portion 5 secures that the web W is fed through the outlet portion 6 in such a way that the first side $W_1$ of the web W is prevented from having any contact with the web guide. Thus, during feeding, instead the second side $W_2$ will temporarily have contact with the envelope surfaces of the rollers 11, 12.

An outer housing 4 surrounds the inner housing 1 and the outer housing 4 is provided with openings forming an inlet 7 and an outlet 8 for the entrance and the exit of the web W.

Figure 5:
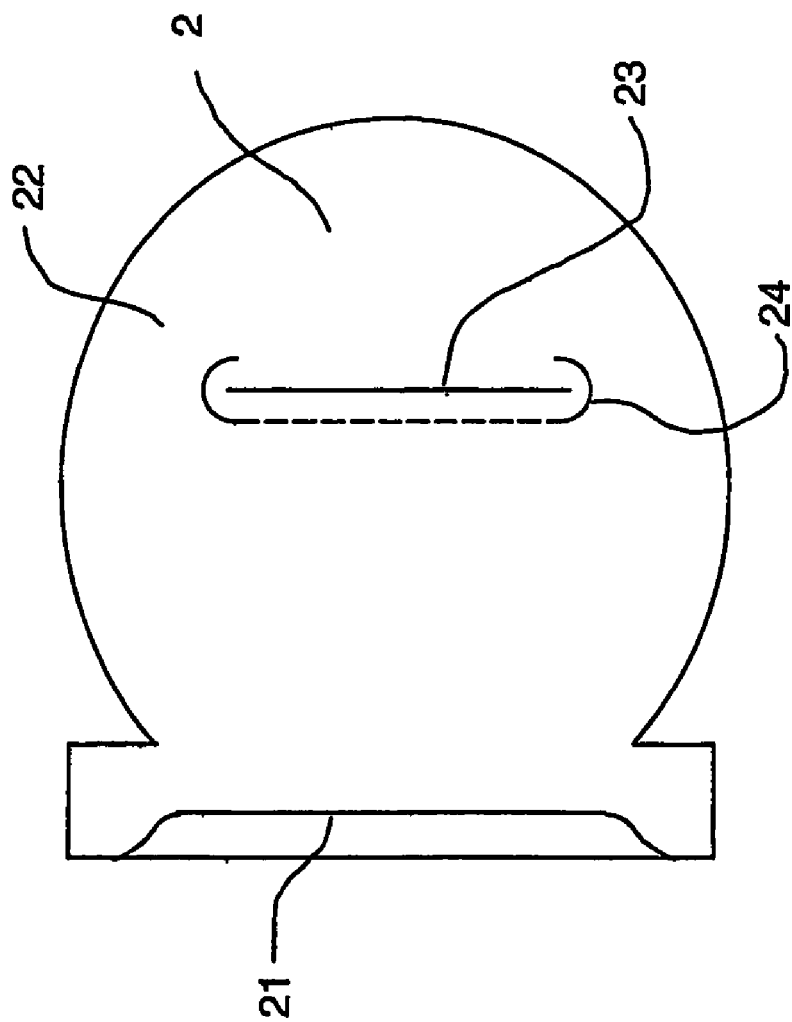
FIG. 5 shows a schematic cross section of an emitter enclosed in the device.

The emitters 2, 3 transmit an electron beam out through the exit windows 21, 31. The emitters are positioned so that the first emitter 2 is adapted to irradiate the first side $W_1$ of the web W and that the second emitter 3 is adapted to irradiate the second side $W_2$. For this purpose the second electron beam emitter 3 is positioned substantially opposite the first emitter 2 and the electron exit window 31 of the second emitter 3 is positioned substantially opposite the first electron exit window 21. Below only the first emitter 2 will be described in more detail. In accordance with the disclosed design, shown in FIG. 5, the emitter 2 generally comprises a vacuum chamber 22 in which a filament 23 and a cage 24 is provided. The filament 23 is made of tungsten. When an electrical current is fed through the filament 23, the electrical resistance of the filament 23 causes the filament 23 to be heated to a temperature in the order of 2000° C. This heating causes the filament 23 to emit a cloud of electrons. A cage 24 provided with a number of openings surrounds the filament 23. The cage 24 serves as a Faraday cage and help to distribute the electrons in a controlled manner. The electrons are accelerated by a voltage between the cage 24 and the exit window 21. The emitters used are generally denoted low voltage electron beam emitters, which emitters normally have a voltage below 300 kV. In the disclosed design the accelerating voltage is in the order of 70-85 kV. This voltage results in a kinetic (motive) energy of 70-85 keV in respect of each electron. The electron exit window is substantially planar and provided substantially in parallell with the web. Further, the exit window 21 is made of a metallic foil and has a thickness in the order of 6 µm. A supporting net formed of aluminium supports the exit window 21. An emitter of this kind is described in more detail in U.S. Pat. No. B1-6,407,492. In U.S. Pat. No. A-5,637,953 is another emitter disclosed. This emitter generally comprises a vacuum chamber with an exit window, wherein a filament and two focusing plates are provided within the vacuum chamber. In U.S. Pat. No. 4,910,435 is yet another emitter disclosed, wherein the electrons are emitted by secondary emittance from a material bombarded by ions. Reference is made to the above patents for a more detailed description of these different emitters. It is contemplated that these emitters and other emitters can be used in the described system.

As long as the electrons are within the vacuum chamber, they travel along lines defined by the voltage supplied to the cage 24 and the window, but as soon as they exit the emitter through the emitter window they start to move in more or less irregular paths (scatter). The electrons are slowed down as they collide with amongst others air molecules, bacteria, the web and the walls of the housing. This decrease of the speed of the electrons, i.e. a loss in kinetic energy, gives rise to the emission of X-rays (roentgen rays) in all directions. The X-rays propagate along straight lines. When such an X-ray hits the inner wall of the housing, the X-ray enters a certain distance into the material and causes emittance of new X-rays in all directions from the point of entrance of the first X-ray. Every time an X-ray hits the wall of the housing and gives rise to a secondary X-ray, the energy is about 700-1000 times less, dependent upon the choice of material for the housing. Stainless steel has a reduction ratio of about 800, i.e. the energy of a secondary X-ray is reduced about 800 times in relation to the primary X-ray. Lead is a material often being considered when radiation is involved. Lead has a lower reduction ratio, but has on the other hand a higher resistance against transmission of the X-rays through the material. If the electrons are accelerated by a voltage of about 80 kV, they are each given a kinetic energy of about 80 keV. In order to secure that the X-rays of this energy level do not pass through the inner housing 1, the inner housing 1 is made of stainless steal having a thickness of 22 mm. Similarly, the inlet and outlet portions are made of stainless steal and, as can be seen in FIG. 1, have substantially the same thickness. Thus, both the walls of the inner housing and of the inlet and outlet portions form a radiation shielding. Any X-ray formed during the electron beam irradiation of the web W is prevented from passing through the walls thereof. This thickness is calculated for X-rays travelling perpendicular to the wall. An X-ray travelling inclined in relation to the wall will experience a longer distance in the wall to reach the same depth, i.e. the wall will appear thicker. The wall thickness is determined by the governmental regulations concerning amount of radiation outside the housing. Today the limiting value that the radiation must be less than is 0,1 µSv/h measured at a distance of 0,1 m form any accessible surface, i.e outside shielding. It should be noted that the choice of material and the dimensions are influenced by the regulations presently applicable and that new regulations might alter the choice of material or the dimensions. The energy of each electron (80 keV) and the number of electrons determine the total energy of the electron cloud. This total energy results in a total energy transfer to the surface to be sterilized. This radiation energy is measured in the unit Gray (Gy). In case of the electron emitter briefly described above (with a filament and Faraday cage) it is presently considered suitable to use a current of about 17 mA through the filament. This is however dependent upon the radiation level decided and the area of the surface to be sterilised. In the present example it is contemplated to sterilise a web with a width of 400 mm travelling with a speed of 35 m/s past the emitter. This will give a radiation energy in the order of 35 kGy on average. In another example the web width is still 400 mm, but the speed that the web is travelling with is increased to 100 m/s. To obtain the same radiation energy, 35 kGy, the current is increased to approximately 50 mA.

In the following the gaseous fluid system of the device will be described. In this embodiment the fluid is sterile air, but it can of course be any gaseous fluid suitable for the field of application in which the device is used.

Figure 6:
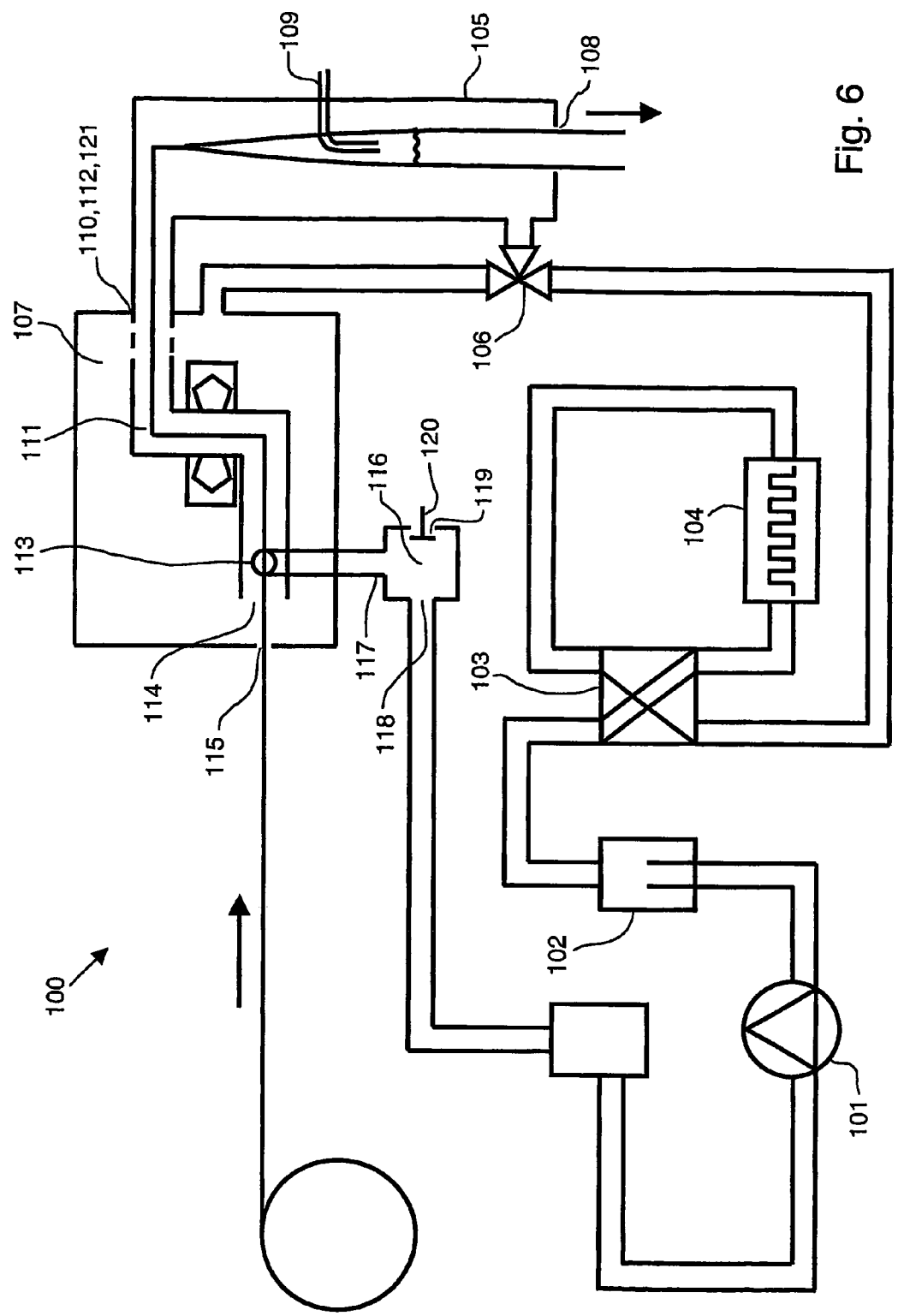
FIG. 6 shows a schematic view of the air system according to the invention.

The air system 100 of the machine, shown in FIG. 6, comprises a compressor 101 and a water separator 102 from which pressurised air is obtained. This air is supplied to a heat exhanger 103 in which the air is pre-heated to about 100° C. From the heat exhanger 103, the air is fed to a superheater 104 in which the air is heated to a temperature within the range 330-450° C. At temperatures above 330° C. any bacteria in the air is killed. The killing rate is dependent upon the temperature and the time the bacteria are subjected to said temperature. The air from the superheater 104 is returned to the heat exhanger 103 for achieving the above-described pre-heating of the incoming air. After the second passage through the heat exchanger 103, the air has a temperature of about 90° C. The air is then fed to a change-over valve 106 having a first branch in fluid connection with the tower 105 of the filling machine and a second branch in fluid connection with a first chamber 107 formed by the outer housing 4. A small amount of the air supplied to the tower 105 will follow the web W out of the tower 105 through an outlet opening 108. In the tower 105 the web W is formed into a tube by overlappingly sealing the longitudinal edges of the web. The tube is continuously filled with a product via a product pipe 109 extending into the tube from the end where the web W has not yet been transformed into a tube. This technology of forming a tube from a web is well known per se and will not be described in detail. The outlet opening 108 is provided with a sealing ring (not shown) in order to have a controlled flow of air out of the outlet opening 108. This can also be achieved by forming the outlet opening 108 with a given clearance in respect of the tube being fed out through the opening 108. The tube is transversally sealed and formed into cushions, which are separated and formed into parallelepipedic containers. Again, this technology is well known per se and will not be described in detail. A significant portion of the air supplied to the tower 105 flows in the tower 105 in a direction opposite the direction of travel of the web W. The tower 105 is provided with a web inlet opening 110 acting as an air outlet opening 110. The air from the tower 105 is fed to a second chamber 111 formed of the inner housing 1.

In the following the area marked with dashed lines in FIG. 6 will be described. The dashed lines represent two alternative embodiments of the air flow into the first and second chambers. In a first embodiment the lines are continuous and represents a closed communication directly between a web outlet opening 112 of the second chamber 111 and a web outlet opening 121, also denoted outlet 8, of the first chamber 107. In a second embodiment the lines are not present and represents an open communication between both the first and second chambers 107, 111 and the web outlet opening 121 of the first chamber 107.

In the first embodiment there is provided a fluid connection between a web outlet opening 112 of the second chamber 111 and a web outlet opening 121 of the first chamber 107. Thus, the air is fed into the second chamber 111 via the web outlet opening 112 acting as an airflow inlet opening 112. The tower 105 acting as a first air supply. If the web outlet opening 112 of the second chamber 111 is located at a distance from and preferably substantially in line with the web outlet opening 121 of the first chamber 107, the fluid connection can for example comprise a pipe that connects the web outlet opening i 12 of the second chamber 111 with the web outlet opening 121 of the first chamber 107. Alternatively, the web outlet opening 112 of the second chamber 111 extends to the web outlet opening 121 of the first chamber 107. A fluid connection between the first chamber 107 and the web outlet opening 121 of the first chamber 107 is thereby prevented. As been earlier described, the change-over valve 106 is acting as air supply 106 for the first chamber 107.

In a second embodiment both the first chamber 107 and the second chamber 111 are in fluid connection with the web outlet opening 121 of the first chamber 107, thus both chambers 107, 111 being in connection with the air supply in the tower 105. In addition, the first chamber 107 is being in contact with valve 106 for additional supply of air.

In both embodiments the air in the second chamber 111 flows in a direction opposite the direction of travel of the web W through the second chamber 111. After passage almost completely through the second chamber 111 the air is fed via a discharge outlet 113 for ultimate disposal of the air. Similarly, the air provided to the first chamber 107 flows in a direction opposite the direction of travel of the web W. The air from the first chamber 107 and the second chamber 111 is discharged via the outlet 113. Thus, both chambers 107, 111 being in contact with the outlet. A small amount of the air supplied to the first chamber 107 escapes via a web inlet opening 115, also denoted inlet 7. The amount escaping is dependent of the shape of the gap and the sealing used. This in turn depends amongst others upon if the web is supplied with pre-applied opening devices or not.

Figure 7:
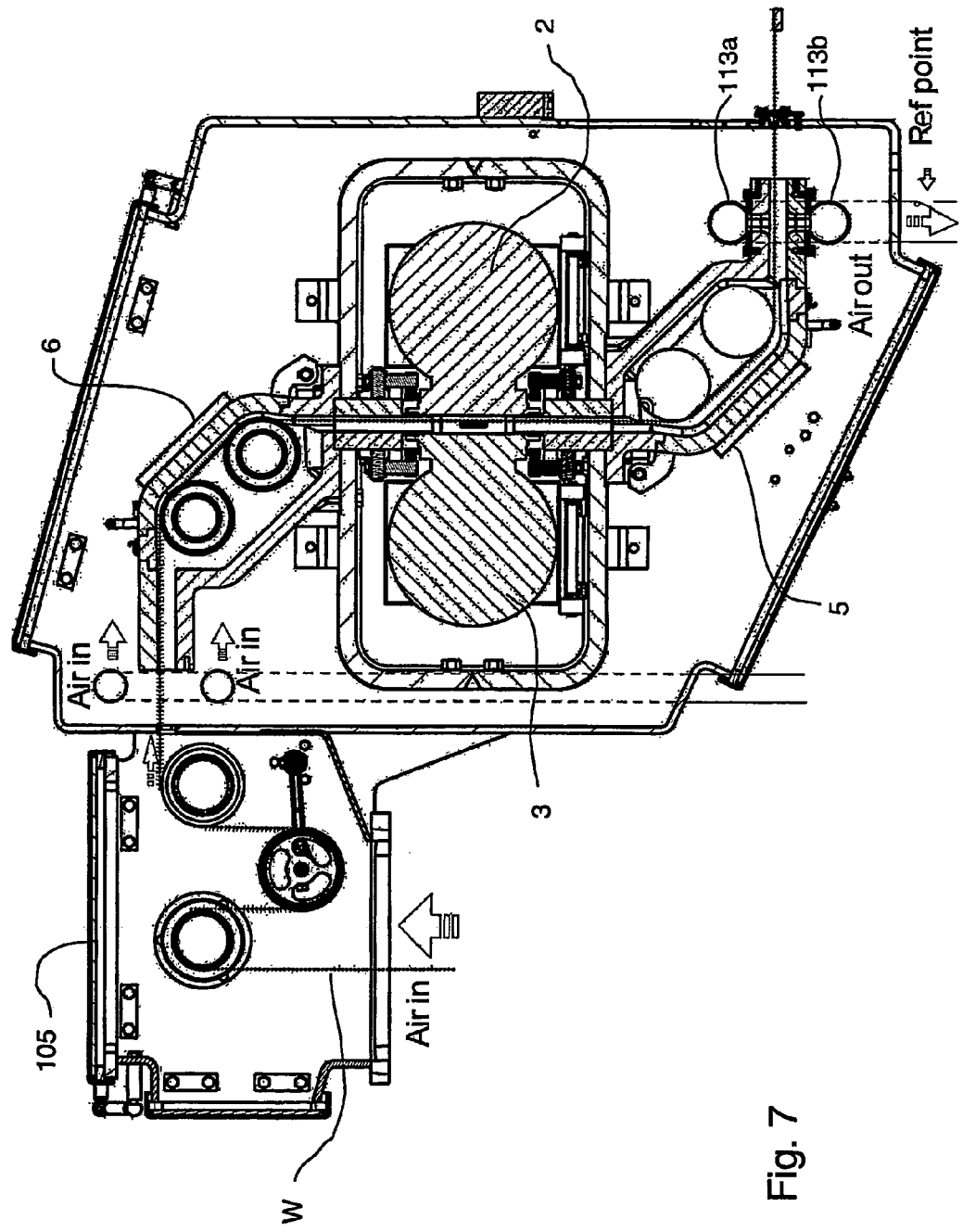
FIG. 7 shows a schematic view like FIG. 1, but shown from the other side and which shows an alternative embodiment.

The discharge outlet 113 is located close to the web inlet opening 114 of the second chamber 111. In FIG. 1, the outlet 113 is located inside the second chamber 111. For example the outlet 113 can be located in the vicinity of the web inlet opening 114 of the second chamber 111. The outlet 113 is discharging almost all the air from the second chamber 111 and most of the air from the first chamber 107. There is provided a fluid connection between the web inlet opening 115 of the first chamber 107 and both the first chamber 107 and the web inlet opening 114 of the second chamber 111. In an alternative embodiment shown in FIG. 7 the outlet 113 comprises two branches 113a, 113b in fluid connection with the second chamber 111. With reference to the figure, the first outlet branch 113a is located in the top of the chamber wall in the vicinity of the web inlet opening 114 of the second chamber 111, and the second outlet branch 113b is located in the bottom wall opposite the first.

The flow of air in the system is controlled so that a first overpressure is created inside the first chamber 107. In the described embodiment the pressure is in the order of 30 mm H$_2$O. Further, a second overpressure is created inside the second chamber 111. The overpressures can for example be choosen so that the first overpressure and the second overpressure are the same. Alternatively, the overpressures are choosen so that the first overpressure and the second overpressure are different. The first pressure can be higher than the second pressure and vice versa. One reason for choosing the first overpressure so that it is higher than the second overpressure is to keep ozone (O$_3$), formed during irradiation, within the second chamber 111 where it can be immediately discharged through the outlet 113. Further, a lower second overpressure helps during pre-sterilization of the device at for example start-up of the machine. By having a lower pressure in the second chamber compared to the first chamber, a sufficient amount of the hydrogen peroxide used during the sterilization is forced inside the second chamber. The pre-sterilization will be explained in more detail below. One reason for choosing the second overpressure so that it is higher than the first overpressure could be to obtain a fast evacuation of ozone and eventual other volatile substances, that for example cause off-flavour, from the second chamber.

Inside the inner housing 1, i.e. around the emitters 2,3, is provided a pressure that is preferably lower than the pressure inside the second chamber 111. One reason for choosing a pressure lower than the pressure inside the second chamber 111 is to minimise the risk of recontamination of the web W by contaminated air contained in the inner housing 1. Since no certain pressure is necessary for the emitters 2, 3 used in this particular embodiment, the pressure in the inner housing 1 can be atmospheric pressure. However, it should be understood that the inner housing 1 may be pressurised if necessitated by the emitters used.

Outside the first chamber 107, the air system 100 is provided with a so-called zero point 116. The zero point 116 is a device making sure that if something fails in the system, any air needed to avoid a pressure below the atmospheric pressure will be fed into the system via the zero point 116. This way it is secured that the pressure inside the tower 105, the first chamber 107 and the second chamber 111 at least not will drop below the atmospheric pressure. The zero point 116 generally comprises a housing with an inlet 117 and an outlet 118 and an opening 119 being closed by a valve 120. Any pressure above the atmospheric pressure pushes the valve outwards sealingly closing of the opening 119. If the pressure inside the zero point 116 drops below the atmospheric pressure the valve 120 will not be pushed against the opening 119 (on the contrary it will be pushed inwards into the zero point 116 and air can be introduced into the system via the opening 119).

During for example start-up of the machine, the air system 100 can be used for sterilizing the surfaces inside of tower 105 and the chambers 107,111 prior to entering the web W. The sterilization is made with hydrogen peroxide ($H_2O_2$). Sterilization using hydrogen peroxide is known per se, but will be briefly described in the following with regard to the air system 100. The tower 105 is in connection with a hydrogen peroxide supply, which is provided with aerosol nozzles. The nozzles feed hydrogen peroxide into the air as spray and the air supplied in the tower is heated to a temperature at which the hydrogen peroxide vapourises, normally a temperature in the order of 40-50° C. The hydrogen peroxide contained air flows through the tower and the chambers 107,111 in the earlier described direction and is discharged at the discharge outlet 113. Along the way the hydrogen peroxide condenses on the surfaces. The hydrogen peroxide is then removed from the surfaces by supplying air of a temperature at or above the hydrogen peroxide vapourisation temperature. In this embodiment a temperature in the order of 70-90° C. is used. By providing a temperture well above the vaporisation temperature the hydrogen peroxide is effectively and quickly removed from the surfaces.

One of the advantages of the gaseous fluid system of the device appears during a stoppage of the filling machine. During a stoppage the web W is stopped and the electron beam emitters 2, 3 in the irradiation device 1 should be turned off not to cause damage to the web W. However, by still continuously providing a flow of sterile air through both the first and second chambers 107, 111 in a direction opposite the direction of travel of the web W, a desired sterilization level can be maintained inside the device 1. Thereby, the desired level of sterilization of the web W is secured and any eventual risk of recontamination thereof is minimised.

In accordance with the method for electron beam irradiation of a web W, the web W is provided to pass through the tunnel. The tunnel is being provided with a web inlet portion 5, a web outlet portion 6 and a central portion adapted to receive an electron beam emitter 2, 3 provided with an electron exit window 21, 31. Electrons are emitted into the tunnel from the emitter 2,3 through the electron exit window 21, 31, and any X-ray being formed by the electrons during irradiation of the web W is forced to hit the tunnel wall twice before exiting the tunnel. To accomplish at least two hits the tunnel is being formed angled at at least two locations in each of the inlet and outlet portions 5, 6.

The web W is guided through the tunnel by at least one web guide provided in each of the inlet and outlet portions 5,6. The web guide in the outlet portion 6 is positioned in such a way with reference to the web W that it is adapted to be in contact with a second side $W_2$ of the web W, and that it is adapted to prevent contact with the first side $W_1$ of the web W.

Further, the method comprises forming the inlet portion 5 so that it comprises a line of three successive segments, an entrance segment 5a, a central segment 5b and an exit segment 5c. The central segment 5b is made so that it forms a first angle $\alpha$ to the entrance segment 5a. Furthermore, the exit segment 5c forms a second angle $\beta$ to the central segment 5b. The outlet portion 6 is similarily designed.

A relation between the tunnel widths, said angles $\alpha,\beta$ and the lengths of the segments 5a-c is formed so that an imagined straight line hitting the tunnel wall in the entrance segment 5a is also hitting the tunnel wall of at least the exit segment 5c, before exiting the exit segment 5c, and that an imagined straight line passing through the entrance segment 5a is hitting the tunnel wall of the central segment 5b such that it is also hitting the tunnel wall of at least the exit segment 5c, before exiting the exit segment 5c.

It is known that during irradiation with electrons ozone ($O_3$) is formed inside the device. Therefore, the invention also comprises a method of ventilating the device. The method comprises the step of providing a first chamber 107 comprising a web inlet opening 115 and a web outlet opening 121. The first chamber 107 being the outer housing 4. A second chamber 111, being the tunnel, is also provided and extends inside the first chamber 107. The second chamber 111 is formed comprising a web inlet opening 114 and a web outlet opening 112. Further, an electron exit window 21, 31 is provided through which electrons are adapted to be emitted into the second chamber 111. The web W is passing through the second chamber 111, and a flow of air through both the first and second chambers 107, 111 is created. The air flow flows in a direction opposite the direction of travel of the web W. The air is supplied into the web outlet opening 121 of the first chamber 107 and there is provided at least one outlet 113.

In an alternative method fluid connection is being provided between the web outlet opening 121 of the second chamber 111 and the web outlet opening 112 of the first chamber 107. At the same time fluid connection between the first chamber 107 and the web outlet opening 121 of the first chamber 107 is prevented. A flow of air through both the first and second chambers 107, 111 in a direction opposite the direction of travel of the web W can then be created by supplying said air into the first chamber 107 and into the web outlet opening 121 of the first chamber 107 and providing at least one outlet 113. Air is supplied to the first chamber 107 through a valve 106 being in fluid connection with the first chamber 107.

According to the method the web W is thus entering the device through the web inlet opening 115 of the first chamber 107 and enters the second chamber 111 at its web inlet opening 114. Both openings 115, 114 are located such that the web W is kept straight, substantially horizontal when passing them. Inside the inlet portion 5 the web W is angled the second angle β at the first roller 9 and angled the first angle α at the second roller 10. During travelling, the web W meets an airflow flowing in a direction opposite the web W. When the web W passes the central portion of the tunnel, now travelling in a vertical direction, it passes electron exit windows 21, 31 through which the web W is irradiated by emitters 2, 3. The electron exit windows 21, 31 are located on opposite sides of the tunnel thereby irradiating both sides of the web W. After the irradiation the web W enters into the outlet portion 6 in which it is angled twice like in the inlet portion 5. Finally, it is exiting the device through the web outlet opening 112 of the second chamber 111, and then through the web outlet opening 121 of the first chamber 107, thereby entering the tower 105.

Although the present invention has been described with respect to a presently preferred embodiment, it is to be understood that various modifications and changes may be made without departing from the object and scope of the invention as defined in the appended claims.

The described embodiment comprises two emitters 2,3, one for electron irradiation of the first side $W_1$ of the web W and the other for electron irradiation of the second side $W_2$ of the web W. However, it is to be understood that the device does not need to comprise two emitters 2,3, but can comprise only the first emitter 2 for irradiation of the side that will be in contact with the product. Further, it has been described that the two emitters 2,3 are located opposite each other. Alternatively they can be located at a distance from each other in the web travelling direction.

Moreover, it is also to be understood that the number of emitters can be more than two. It is for example possible to have several emitters side by side to handle wide webs. It is also possible to have two or more emitters located after each other along the web travelling direction to form either subsequent sterilizing zones which together provide the decided radiation level, or as measure of selective radiation of a certain point, for example a closure device, that may need a higher radiation level.

The web guides described are bending rollers. However, it should be understood that web guides do not need to be bending rollers but could be any other means suitable for guiding the web through the tunnel.

Further, it should be understood that the location of the outlet 113 can be modified. In the above-described emodiment the outlet 113 is located inside the second chamber 111. Alternatively the outlet 113 can for example be located in vicinity of the web inlet opening 114 of the second chamber 111 or in the vicinity of the web inlet opening 115 of the first chamber 107. It is also possible to locate the outlet 113 outside, near the inlet opening 115, of the first chamber 107.

Moreover, in the above-described embodiment the outlet 113 is located inside the second chamber 111 and the first chamber 107 is in fluid connection with the second chamber 111. In an alternative embodiment the web inlet opening 114 of the second chamber 111 is in fluid connection with the web inlet opening 115 of the first chamber 107, while fluid connection between the first chamber 107, its web inlet opening 115 and the web inlet opening 114 of the second chamber 111 is prevented. The two chambers 107,111 will then be in communication with separate outlets. At least one outlet can be located in the first chamber 107 and at least one outlet can be located in the second chamber 111 or in fluid connection with the second chamber 111.

Further, the air system described using hydrogen peroxide is preferably used in aseptic fields of application. In a corresponding air system in a packaging machine used for handling pasteurized products the air flows are similar, although the machine sterilization is usually made by using filtered air. Instead of the above described system, the system can then comprise a filter and a fan. To evacuate ozone from the chambers during operation, the system can be provided with a catalytic converter.

Moreover, in the embodiment shown the web inlet opening 114 of the second chamber 111 is located at a distance from and preferably in line with the web inlet opening 115 of the first chamber 107. Alternatively, the second chamber 111 can extend all the way up to the web inlet opening 115 of the first chamber thereby preventing fluid connection between the first chamber 107 and the web inlet opening 115. The wall of the second chamber 111 is then instead provided with throughgoing openings, preferably slits, at a distance from the web inlet opening, but before the outlet 113. Fluid connection between the two chambers is thereby provided and the arrangement give rise to a so called injector effect making air flow from the first chamber through the slits into the second chamber where it can be evacuated through the outlet 113. A small amount of air is also sucked from outside the housings through the web inlet opening 115.

The invention claimed is:

1. Device for electron beam irradiation of at least a first side of a web, the device comprising a tunnel through which the web is adapted to pass, said tunnel being provided with a web inlet portion, a web outlet portion and a central portion adapted to receive at least a first electron beam emitter provided with an electron exit window through which electrons are adapted to be emitted into the tunnel, and whereby the tunnel is angled at at least two locations in each of the inlet portion and the outlet portion in such a way that any X-ray formed during the electron beam irradiation of the web is forced to hit the tunnel wall at least twice before exiting the tunnel.

2. Device according to claim 1, whereby the inlet portion and the outlet portion respectively comprises three successive segments, an entrance segment, a central segment and an exit segment, and whereby the central segment forming a first angle to the entrance segment and the exit segment forming a second angle to the central segment.

3. Device according to claim 2, whereby the relation between the tunnel widths, said angles and the lengths of the segments is such that an imagined straight line hitting the tunnel wall in the entrance segment also hits the tunnel wall of at least the exit segment, before exiting the exit segment, and that an imagined straight line passing through the entrance segment hits the tunnel wall of the central segment such that it also hits the tunnel wall of at least the exit segment, before exiting the exit segment.

4. Device according to claim 1, whereby the central portion is adapted to receive an additional second electron beam emitter provided with an electron exit window through which electrons are adapted to be emitted into the tunnel, the electron beam emitter being adapted to be positioned so that a second side of the web is being irradiated by the electrons.

5. Device according to claim 1, whereby the electron exit window is substantially planar and adapted to be provided substantially in parallel with the web.

6. Device according to claim 4, whereby the additional second electron beam emitter being adapted to be positioned substantially opposite the first electron beam emitter and the electron exit window being adapted to be positioned substantially opposite the first electron exit window.

7. Device according to claim 1, whereby the emitter is enclosed in a housing.

8. Device according to claim 1, whereby the emitter is a low voltage electron beam emitter.

9. Device according to claim 1, whereby the inlet and outlet portions are each provided with at least one web guide for guiding the web through the tunnel.

10. Device according to claim 9, whereby the at least one web guide in the outlet portion is positioned in such a way with reference to the web that it is adapted to be in contact with a second side of the web, and that it is adapted to prevent contact with the first side of the web.

11. Device according to claim 9, whereby the web guide comprises a first and a second roller journalled in support members, the rollers being formed and mutually located in such a way that the first roller angles the web the second angle and that the second roller angles the web the first angle.

12. Device according to claim 2, whereby the entrance segment of the inlet portion and the outlet portion are adjacent the central portion of the tunnel and that the exit segment of the inlet portion and the outlet portion are directed away from each other.

13. Device according to claim 2, whereby the tunnel portions and the emitter housing are enclosed in a housing.

14. Method for electron beam irradiation of at least a first side of a web, the method comprising:
    passing the web through a tunnel, said tunnel being provided with a web inlet portion, a web outlet portion and a central portion adapted to receive at least a first electron beam emitter provided with an electron exit window,
    emitting electrons into the tunnel from the emitter through the electron exit window, and
    forcing any X-ray being formed by the electrons during irradiation of the web hit the tunnel wall at least twice before exiting the tunnel by forming the tunnel so that it is angled at at least two locations in each of the inlet and outlet portions.

15. Method according to claim 14, forming the inlet portion and the outlet portion so that the respective portion comprises a line of three successive segments, an entrance segment, a central segment and an exit segment, the central segment is made so that it forms a first angle to the entrance segment and so that the exit segment forms a second angle to the central segment.

16. Method according to claim 15, providing a relation between the tunnel widths, said angles and the lengths of the segments so that an imagined straight line hitting the tunnel wall in the entrance segment is also hitting the tunnel wall of at least the exit segment, before exiting the exit segment, and that an imagined straight line passing through the entrance segment is hitting the tunnel wall of the central segment such that it is also hitting the tunnel wall of at least the exit segment, before exiting the exit segment.

17. Device according to claim 2, whereby the electron exit window is substantially planar and adapted to be provided substantially in parallel with the web.

18. Device according to claim 3, whereby the electron exit window is substantially planar and adapted to be provided substantially in parallel with the web.

19. Device according to claim 4, whereby the electron exit window is substantially planar and adapted to be provided substantially in parallel with the web.

20. Device according to claim 5, whereby the additional second electron beam emitter is adapted to be positioned substantially opposite the first electron beam emitter and the electron exit window being adapted to be positioned substantially opposite the first electron exit window.

* * * * *